United States Patent
Yang et al.

(10) Patent No.: US 8,425,683 B2
(45) Date of Patent: Apr. 23, 2013

(54) METHOD FOR TRACKING A SCRAPER WITHIN A PIPELINE

(75) Inventors: Bao-Wen Yang, Closter, NJ (US); Eric Yang, Closter, NJ (US); Marion Recane, Cypress, TX (US); Stephanie H. Yang, Closter, NJ (US)

(73) Assignees: Acoustic Systems, Inc., Houston, TX (US); Acoustic Systems, Inc., Nanuet, NY (US)

( * ) Notice: Subject to any disclaimer, the term of this patent is extended or adjusted under 35 U.S.C. 154(b) by 503 days.

(21) Appl. No.: 12/719,350

(22) Filed: Mar. 8, 2010

(65) Prior Publication Data

US 2011/0114119 A1    May 19, 2011

Related U.S. Application Data

(60) Provisional application No. 61/261,898, filed on Nov. 17, 2009.

(51) Int. Cl.
*B08B 3/12* (2006.01)
*B08B 9/04* (2006.01)

(52) U.S. Cl.
USPC ..................... 134/1; 134/8; 134/42

(58) Field of Classification Search .............. 134/8, 42; 73/40.5 R, 440.5 A, 861.16, 861.23, 861.24, 73/861.27, 865.8, 587
See application file for complete search history.

(56) References Cited

U.S. PATENT DOCUMENTS

| | | | |
|---|---|---|---|
| 4,677,865 A | 7/1987 | Lehmann | |
| 4,798,246 A | 1/1989 | Best | |
| 5,035,021 A | 7/1991 | Le Devehat | |
| 5,358,573 A | 10/1994 | Sivacoe | |
| 5,528,790 A | 6/1996 | Curran | |
| 5,600,862 A | 2/1997 | Bleske et al. | |
| 5,685,041 A | 11/1997 | Sivacoe | |
| 6,389,881 B1 | 5/2002 | Yang et al. | |
| 6,668,619 B2 | 12/2003 | Yang et al. | |
| 6,965,320 B1 * | 11/2005 | Casey et al. | 340/870.07 |
| 2004/0261547 A1 * | 12/2004 | Russell et al. | 73/865.8 |
| 2009/0013806 A1 * | 1/2009 | Miller et al. | 73/865.8 |

* cited by examiner

*Primary Examiner* — Saeed T Chaudhry
(74) *Attorney, Agent, or Firm* — Egbert Law Offices, PLLC

(57) ABSTRACT

A method for tracking a scraper within a pipeline has the steps of moving the scraper along a path in the pipeline such that the scraper produces an acoustic signal, sensing the acoustic signal as produced by the scraper by at least a pair of acoustic sensors positioned in spaced relation along the pipeline, time-stamping the sensed acoustic signal, and calculating a location of the scraper based on the time-stamped acoustic signal. The acoustic signal can be a transient pressure wave produced by the movement of the scraper or a pressure signal produced by a mechanism positioned on the scraper.

3 Claims, 4 Drawing Sheets

METHOD FOR TRACKING A SCRAPER WITHIN A PIPELINE

RELATED U.S. APPLICATIONS

The present application claims priority from prior-filed U.S. Provisional Patent Application Ser. No. 61/261,898, filed on Nov. 17, 2009.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to pipeline cleaning systems. More particularly, the present invention relates to tracking systems for pipeline cleaning scrapers which travel inside the pipeline propelled by a cleaning fluid injected at the end of the pipeline.

2. Description of Related Art Including Information Disclosed Under 37 CFR 1.97 and 37 CFR 1.98

Scrapers, also known as pigs, are pieces of pipe where elastomer discs are attached radially at various points along the pipe. The elastomer discs of the scraper slide along the internal wall of the pipeline and remove the adhered corrosion and other undesired substances.

Accumulated material adhered on the pipeline internal wall can obstruct passage of the scraper. This produces a stick-slip motion of the scraper in the areas where its mobility is reduced. In some cases, the inside pipeline diameter contour loses circularity, increasing heavily the drag forces acting on the scraper. The scraper reduces speed and is eventually stopped. In other cases, the operating pressure, when launching and pushing the scraper through the pipeline, may drop to undesirable levels at certain points along the pipeline causing the scraper to get stuck or lose momentum. The various changes in scraper speed while it travels along the pipeline make it difficult to detect and locate by pressure monitoring systems, or other flowrate and pressure drop modeling systems.

Various patents have issued in the past relating to pipe scrapers or pigs. For example, U.S. Pat. No. 4,798,246, issued on Jan. 17, 1989 to Best, describes a pipe scraper. The pipe scraper has scraper blades having arcuate scraper surfaces projecting therefrom. The blades are movable radially between a contracted and expanded position which provides a first minimum diameter of the scraper surfaces in contracted position and a second maximum diameter when in expanded position which extends at least to the maximum internal pipe diameter. An adjustment arrangement enables the arcuate scraper blades to be adjusted radially to maintain the first and second diameters as the scraper surfaces wear.

U.S. Pat. No. 5,600,862, issued on Feb. 11, 1997 to Bleske et al., teaches a pipe scraper. The pipe scraper is for removing a uniform amount of material from the perimeter of a pipe. The pipe scraper has a shoulder and biased members for urging the pipe against an interior surface of the scraper body to achieve a uniform scrape with both round and oval pipes, without a need for blade adjustment. Uneven scraping due to canting of the pipe with respect to the body is also eliminated.

U.S. Pat. No. 5,528,790, issued on Jun. 25, 1996 to Curran, describes another pipe scraper assembly. The pipe scraper assembly is forced through condenser pipe interiors for scraping residue off the inner wall surface. The scraper assembly is formed with a cylindrical body with a head and a tail end. Several mutually spaced apart rings are coaxially and rotatably supported on the cylindrical body between the head and the tail end. The diameter of the rings corresponds to the inner diameter of the pipe to be scraped. The rings have a radial cut formed therein which extends obliquely relative to the longitudinal axis of the cylindrical body.

U.S. Pat. No. 5,035,021, issued on Jul. 30, 1991 to Le Devehat, teaches a scraper for liquid distribution pipes, particularly for petroleum products. The pipeline scraper has an elongated body defined by two complementary parts that form end portions and a reduced cross-section central portion, two wear segments surrounding and mounted on the central portion adjacent the end portions, and threaded means releasably fastening the components together.

U.S. Pat. No. 4,677,865, issued on Jul. 7, 1987 to Lehmann, describes a pipe pig with running gear. The pipe pig is supported on and moved by two or three runners, which also can move circumferentially on the inside of the pipe to alter the angular position of the runners with respect to the longitudinal axis of the pipe. In this way the runners, which support the pipe pig by contact with the inside surface of the pipe, may rotate so as to avoid obstructions as they are encountered. Such obstructions may take the forms of openings in the pipe wall or protrusions into the pipe from the pipe wall. Various devices may be used to detect the presence of such obstacles and to detect both the axial position and angular orientation of the pig within the pipe. The apparatus for changing the angular position of the runners may be integrated with or separate from the apparatus for moving the pig axially in the pipe.

U.S. Pat. No. 5,358,573, issued on Oct. 25, 1994 to Sivacoe, describes a method of cleaning a pipe with a cylindrical pipe pig having pins in the central portion. The pipe pig is reciprocated through a section of a pipe having deposits of scale. In the case of very hard deposits, each pass through the contaminated sections removes a thin layer each time. The location of the coated section can be located by first running the pig through the pipe. The hydraulic pressure is monitored using pen recorders. At each bend in the pipe, a sharp pressure increase will be recorded. The location of the bends can be determined from a drawing of the pipe installation. When the pig encounters scale, there will be a pressure increase that corresponds to the degree of resistance met by the pig resulting from the scale. Greater pressure means greater scale buildup. By running the pig through the pipe, a profile of the scale may be created. The location of the scale can be correlated to the known location of the bends. The scale itself can be flushed out with the hydraulic propellant and analyzed. The pin height and hardness can then be selected for the particular scale encountered. The pig may be run backwards and forwards primarily through the contaminated section. After several passes, the pig can be removed from the pipe, the pins replaced or moved radially outward by placing washers between at least some of the pins and the pig body and the pig returned to the pipe.

U.S. Pat. No. 5,685,041, issued on Nov. 11, 1997 to Sivacoe, teaches a pipe pig with an abrasive exterior. Additionally, the patent teaches a method of making a rotationally symmetric pipe pig in which porous abrasive material is adhered to the periphery of the pipe pig. A liquid applied surface layer of the pig body forms an adhesive for the porous abrasive material, which is cured after the application of the porous abrasive material. The porous abrasive material is alumina ceramic beads. The pipe pig thus formed has a porous abrasive material adhered to the periphery of the pipe pig.

Various patents have issued in the past relating to acoustic leak detection in pipelines. Leak detection technology may be used in conjunction with scraper technology of the present invention. One of the present inventors is the inventor of several patents in the field. For example, U.S. Pat. No. 6,389,881 issued on May 21, 2002 to Yang, et al. describes a method and apparatus for pattern match filtering for real time acoustic pipeline leak detection and location. The patent describes how pattern match filtering is used to reduce false alarm rate, increase sensitivity and improve leak location accuracy, while quickly detecting leaks by the acoustic signal generated from a leak event in pipelines containing gas or liquid under pressure. The pattern match filter technique detects a pressure wave generated by a leak, but discriminates against background noise and pressure disturbance generated by other non-leak sources that might otherwise be detected as a leak. The pattern match filter derives a sharp peaked output from the signal of the expansion wave which allows for a distinctive point of reference for a time stamp. This provides for improved accuracy in leak location calculations. The pattern match filter is incorporated into site processors located at multiple points along a pipeline, and at a central node processor which receives data from all site processors, performs further evaluation and identification, as well as scraper position and speed calculation. The pattern match filter includes using previously recorded leak profiles. At site processes located at multiple points along a pipeline, a series of previously recorded signature profiles are continuously compared in real time against pipeline pressure signals. Data from each site processor are used collectively at a node processor and compared against multiple leak profiles to provide further false alarm rejection. The leak event data generated at each site processor is used by the node processor to declare a leak. By the application of this pattern match filter technique, the signal to noise ratio (S/N ratio) required to identify a leak event is reduced and the sensitivity of leak detection is increased. U.S. Pat. No. 6,668,619 issued to Yang et al. on Dec. 30, 2003 describes a related method of pattern match filtering.

The difficulties in determining position and speed of the scraper as it travels along the pipeline reside also on the inherent limitations of radio frequency transmitters in reaching, from the inside of a metallic pipe, a few tens of meters away from the pipe wall. This limitation imposes the need for utilizing multiple signal receivers placed outside the pipe wall at regularly spaced intervals and sufficiently close to the pipeline in order to ensure proper reception of the signal transmitted by the scraper built-in transmitters.

Therefore, what is needed is a system capable of measuring and accurately determining position and speed of the scraper traveling inside a metallic pipe.

It is an object of the present invention to provide a system for tracking scrapers as they move along a pipeline.

It is another object of the present invention to provide a scraper tracking system which utilizes acoustic pressure sensors and data processors.

It is yet another object of the present invention to provide a scraper tracking system which accurately and precisely locates scrapers.

It is another object of the present invention to provide a scraper tracking system which can determine the speed of a scraper moving through a pipeline.

It is a further object of the present invention to provide a scraper tracking system that can be used in conjunction with current acoustic sensor technology.

It is another object of the present invention to provide a scraper tracking system that utilizes pattern recognition techniques such as previously developed pattern techniques described in U.S. Pat. No. 6,668,619, neural network-based approaches, or other methods to identify the unique acoustic pressure wave pattern emitted a signal generator contained within the scraper.

It is yet another object of the present invention to provide a scraper tracking system that utilizes pattern recognition techniques such as previously developed pattern techniques described in U.S. Pat. No. 6,668,619, neural network-based approaches, or other methods to identify the unique local pressure transient profile associated with the passing of the scraper and its incoming and departing dynamics.

These and other objects and advantages of the present invention will become apparent from a reading of the attached specification and appended claims.

BRIEF SUMMARY OF THE INVENTION

The present invention is a tracking system for use with a pipeline including a scraper having signal generating means for generating an acoustic signal. The scraper has a size suitable for fitting within and travelling in a path along the pipeline. A plurality of acoustic pressure sensors are positioned at intervals along the path travelled by the scraper. The plurality of acoustic pressure sensors are suitable for sensing the acoustic signal from said scraper. A plurality of local processors are positioned at intervals along the path travelled by the scraper and each of the plurality of local processors are in communication with a respective acoustic pressure sensor of the plurality of acoustic pressure sensors. A central processor is in communication with the plurality of local processors. The central processor is suitable for generating an output indicative of a location of the scraper within the pipeline.

In the present invention, each of the plurality of local processors have a GPS unit thereon suitable for time-stamping the acoustic signal received by the acoustic pressure sensor. In one embodiment of the present invention, the signal generating means of said scraper includes at least one fluid intake nozzle positioned on an end of the scraper, a reservoir tank positioned interior of the scraper and in communication with the at least one fluid intake nozzle, a pump positioned interior of the scraper in communication with the reservoir tank, and a pressure relief valve in communication with the pump and an exterior of the scraper. The pressure relief valve is suitable for releasing fluid from the reservoir tank to produce a positive-negative pressure wave. The signal generating means of the scraper may further include at least one vibrating plate positioned within the scraper.

In one embodiment of the present invention, the scraper further includes a scraper body, a battery positioned interior of the scraper body, a control system positioned interior of the scraper body, a reservoir tank positioned interior of the scraper body; a pump positioned interior of the scraper body and in communication with the reservoir tank, and a scraper cover positioned on one end of the scraper body. The scraper cover includes a plurality of fluid intake nozzles in communication with the exterior of the scraper, at least one filter unit positioned interior of the fluid intake nozzles, and a pressure relief valve in communication with the pump and the exterior of the scraper. The pressure relief valve is suitable for releasing fluid from the reservoir tank to produce a positive-negative pressure wave. The plurality of fluid intake nozzles may be spaced apart on at least two nozzle islands which are separated by an elastomeric joint.

In an alternative embodiment of the present invention, the signal generating means of the scraper further includes a nitrogen tank contained within the scraper, and a pressure relief valve in communication with the nitrogen tank and the exterior of the scraper. The pressure relief valve is suitable for releasing fluid to produce a positive-negative pressure wave.

In another alternative embodiment of the present invention, the signal generating means of the scraper further includes an air compressor contained within said scraper, and a pressure relief valve in communication with the air compressor and the exterior of the scraper. The pressure relief valve is suitable for releasing fluid to produce a positive-negative pressure wave.

In one embodiment of the present invention, the central processor is suitable for producing an output indicative of a leak in the pipeline.

The present invention is also a trackable pipeline scraper including a scraper body having a generally cylindrical shape, a scraper cover on one end of the scraper body, and a signal generating means positioned within the scraper body adjacent the scraper cover, the signal generating means for generating acoustic pressure signals. The signal generating means may include at least one fluid intake nozzle positioned on the scraper cover, a reservoir tank positioned interior of the scraper body, and in communication with the at least one fluid intake nozzle, a pump positioned interior of the scraper body and in communication with the reservoir tank, and a pressure relief valve in communication with the pump and an exterior of the scraper. The pressure relief valve is suitable for releasing fluid from the reservoir tank to produce a positive-negative pressure wave. The signal generating means may further include at least one vibrating plate positioned within the scraper body. The trackable pipeline scraper may further include a battery positioned interior of the scraper body, and a control system positioned interior of the scraper body and connected to said battery. The signal generating means may further include at least one filter unit positioned interior of the at least one fluid intake nozzle. The at least one fluid intake nozzle may include a plurality of fluid intake nozzles being spaced apart on at least two nozzle islands. The at least two nozzle islands may be separated by an elastomeric joint.

The present invention is also a method for tracking a scraper within a pipeline including the steps of: moving the scraper along a path in the pipeline such that the scraper produces an acoustic signal, sensing the produced acoustic signal by at least a pair of acoustic sensors positioned in spaced relation along the pipeline, time-stamping the sensed produced acoustic signals, and calculating a location of the scraper based on the time-stamped sensed produced acoustic signal and a velocity of sound in the fluid in the pipeline. The acoustic signal may be a transient pressure wave produced by the movement of the scraper. The acoustic signal may also be a pressure signal produced by a mechanism positioned on the scraper.

DETAILED DESCRIPTION OF THE INVENTION

Figure 1:
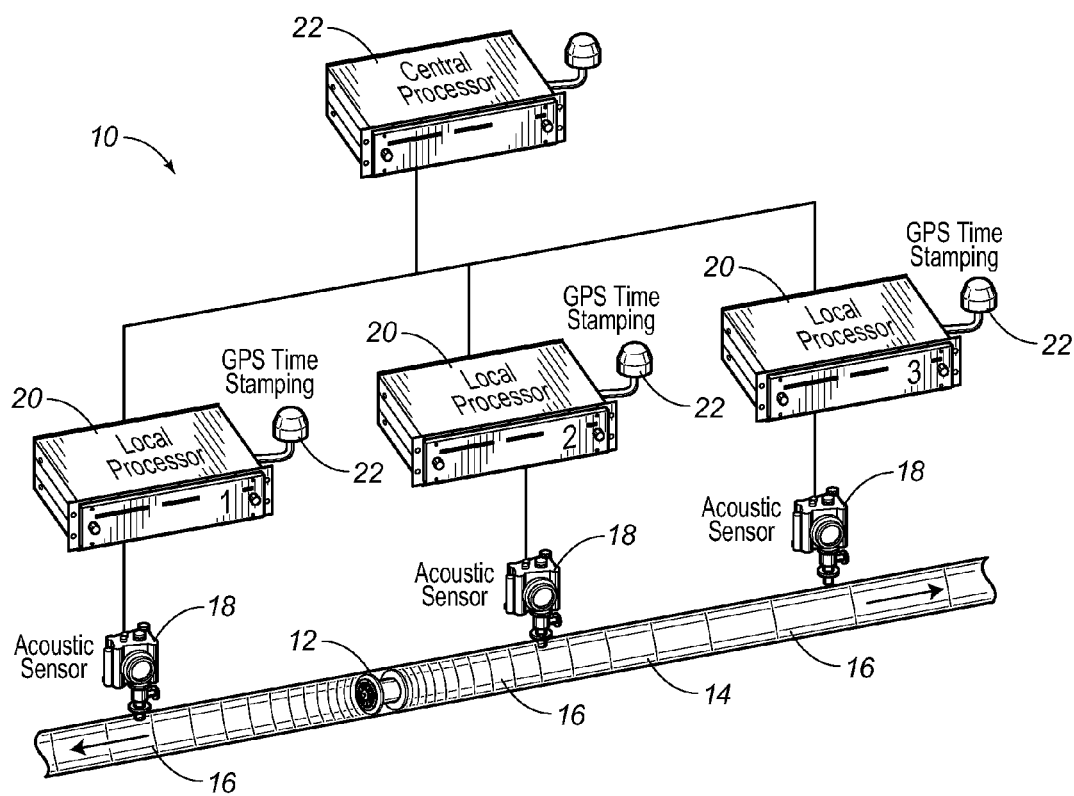
FIG. 1 is a schematic view showing the system of the preferred embodiment of the present invention.

Referring to FIG. 1, there is shown the scraper tracking system 10 of the preferred embodiment of the present invention. The system 10 has a scraper 12 equipped with an acoustic signal generator capable of generating a predefined pressure wave pattern that travels through the pipeline 14 at the speed of sound in both directions. The acoustic generator has nozzles placed on both sides of the scraper 12 in such a way that opposite direction pressure waves travel from the scraper 12 as it moves across the pipeline.

As shown in FIG. 1, the scraper-generated acoustic pressure waves 16 travel tens of kilometers away from the scraper 12 until acoustic pressure sensors 18 located upstream and downstream detect the wave 16 and apply time stamping based on synchronized time from the GPS unit 22 at each location. The pressure wave 16 travels across the pipeline fluid producing a pressure peak which is detected by the sensors 18 and field or local processors 20. Alternatively, the pressure wave 16 can be generated by the vibrating plates which can displace much larger signals. Alternatively, a unique pressure transient pattern can be generated hydraulically as a result of the pressure wave 16 generated by the vibrating plates which can displace much larger signals. The acoustic pressure waves 16 are shown in FIG. 1 as curved lines extending generally perpendicular to the pipeline 14 and travel in the direction of the arrows pointing away from the scraper 12. As described in U.S. Pat. No. 6,389,881, the methodology used in acoustic leak detection may be applied in the present invention for scraper tracking. The acoustic pressure wave data obtained by the local sensors 18 is processed and analyzed for effective positive identification of the acoustic signals generated by the scraper 12. Local processors 20 are connected to the various acoustic sensors 18 and perform the initial processing. The on-line real-time signals recognition process may be performed by a previously trained neural network data process scheme or by similar pattern recognition algorithm used in the acoustic leak detection system of U.S. Pat. No. 6,389,881 to detect specific families of pressure patterns produced by the scraper wave generator or as a unique pressure transient pattern generated locally as the travelling scraper passes a particular acoustic sensor.

While the system 10 may be used with previously developed acoustic leak detection systems, it may also be a stand-alone system whereby the various components are solely dedicated to tracking of the scraper 12. The generated wave pattern may have different frequencies depending on several variables including: the type of pipe, the fluid in the pipe, the number of turns and bends or other potential obstructions in the pipeline, and the span between sensors 18. For example, a lower frequency may be used where the distance between sensors is great. The system 10 and the associated frequency may be optimized for desired accuracy. In the case of a pipeline with a high number of bends, more sensors 18 may be utilized.

The neural network or other pattern recognition algorithm runs in a local processor 20, which provides time synchronization, through the highly accurate GPS time stamping, and high-speed computing power required for running on-line real-time pattern recognition functions.

Once the wave pattern is recognized and the results are time stamped, consisting in a flag register formed by a plurality of bytes indicating if the wave pattern has been detected, the pattern wave threshold used for detection, the signal quality by the signal-to-noise ratio, the confidence level for pattern recognition, the degree of matching, and the time stamp, are sent to a central processor 22 which performs speed calculation and location.

The central processor 22 determines the location of the scraper 12. First, at any point in time when the scraper 12 passes by a pressure sensor, the central processor 22 receives a series of consecutive flag registers from the adjacent local processors 20 and determines the speed of sound in the segment where the scraper 12 is passing by calculating the average speed. Average speed is calculated by computing the average travel distance and the differential arrival times at a certain sensor between the actual time of arrival and the expected arrival time with zero flow speed This calculation is performed at both sensors upstream and downstream of the scrapers to obtain the averaged measured value In the preferred embodiment of the system 10 of the present invention, the user can set the number of time-stamped signals emitted from the scraper and the time interval between signals, and can program when the average speed calculation algorithm starts whether at every pressure sensor 18 or at pre-determined points along the pipeline 14. This feature allows reaching higher levels of accuracy in scraper location and average sound speed calculation. Next, the central processor 22 determines the location of the scraper 12 by referencing the distance between the sensors 18 and the calculated speed.

Figure 2:
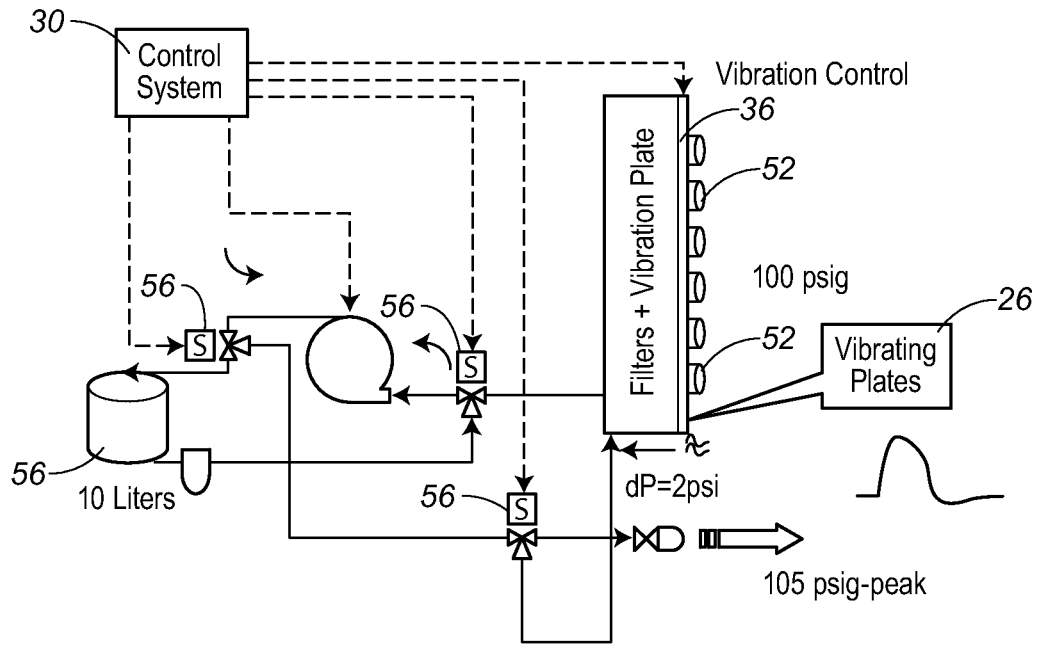
FIG. 2 is a schematic view showing the scraper of the present invention.
Figure 3:
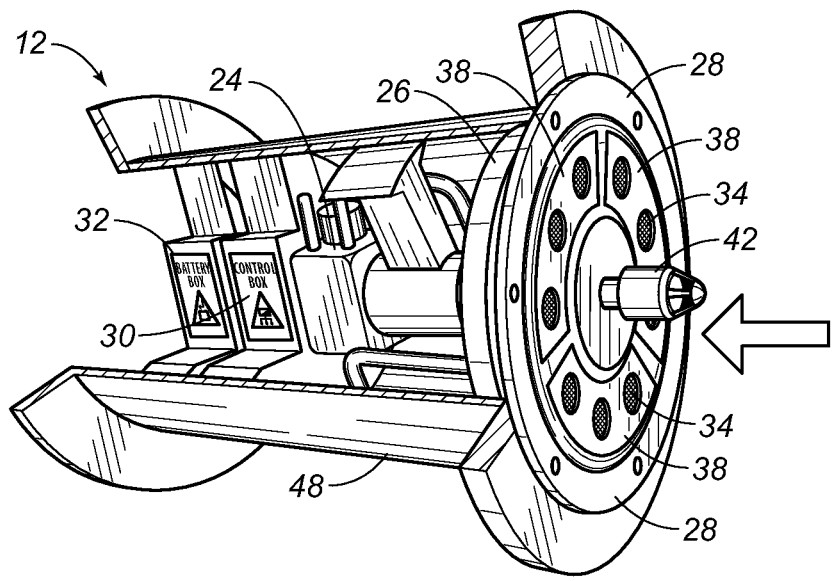
FIG. 3 is a perspective view showing the scraper of the present invention.

Referring to FIGS. 2 & 3, the scraper 12 is equipped with a high pressure pump 24 and a vibrating plate 26 capable of producing a distinctive positive-negative pressure wave by releasing fluid from a fast-acting pilot operated pressure relief valve 42 positioned at the center of the scraper cover 28.

As shown in FIGS. 2 and 3, in a liquid line, the scraper 12 is equipped with a high pressure pump 24 (in the gas pipeline version comes with a nitrogen tank or air compressor) which is installed in an explosion proof enclosure. The controller 30, the pump 24 and the solenoid valves 56 are installed in explosion proof enclosures as well. All of the electrical components are powered by a maintenance-free battery 32 installed in one end of the scraper 12, which also placed in explosion proof enclosure.

Under the pump 24, a reservoir tank 56 stores the liquid suctioned from the fluid intake nozzles 34 (shown in FIGS. 3 and 5) through the filter chamber 36. The scraper 12 has nine nozzles 34 connected to a filter chamber 36 filled with coalescent filters of fifty microns. The filters are intended to capture large size particles that may damage the pump 24.

The sequence of operation of the scraper tracking system 10 is described below. The scraper 12 is placed in a scraper launcher and a kicker valve is opened to launch the scraper 12 into the pipeline 14. The fluid pushes the scraper 12 through the pipeline 14. The scraper pump 24 suctions the fluid from the reservoir tank 56 installed below the pump 24. The tank fluid is initially suctioned by the pump 24 through the nozzles 34 drilled in the scraper cover 28. The nozzles 34 are preferably one inch in diameter. The nozzles 34 are separated in three islands 38 of three nozzles 34 each. The fluid is suctioned through coalescent filters 52. A total of ten liters is suctioned. This amount is sufficient to produce at least two pressure waves for every thirty kilometers of pipeline.

After every suction through the intake nozzles 34, which are placed in three metallic islands 38 supported by elastomeric joints 40, the nozzles 34 vibrate to release any possible solid material trapped in the nozzle grid. The nozzle islands 38 can move slightly in the longitudinal axis of the scraper 12 in order to produce slight movement of the fluid. At the center of the scraper cover 28 there is a pop pilot operated relief valve 42 of fast action.

After the reservoir tank 56 reaches maximum level, the pump 24 starts and increases discharge pressure approximately by a designed pressure of about 2 to 5 psi. Upon reaching the designed pressure, the relief valve 42 is triggered to produce a controlled discharge of the fluid into the pipeline 14 producing a pressure wave 16. The vibrating plates surrounding the nozzles 34 produce a reflecting pressure wave front just at the time when the fluid is released from the relief valve 42.

The scraper cover 28 is made of steel and bolted onto the scraper body 48. A gasket between the cover 28 and scraper body 48 ensures tightness and protection of the internal parts. The cover 28 has three metallic islands 38 supported by an elastomeric joint 40. The metallic islands 38 can move slightly and vibrate. The vibration is used to remove solids trapped into the nozzle covers and to generate different types of pressure waves. Each island 38 is equipped with three nozzles 34 that connect to a filter chamber filled with coalescent filters 52 of fifty microns. The joint 40 between the nozzles 34 and the metallic islands 38 is made of an elastomeric material.

Figure 4:
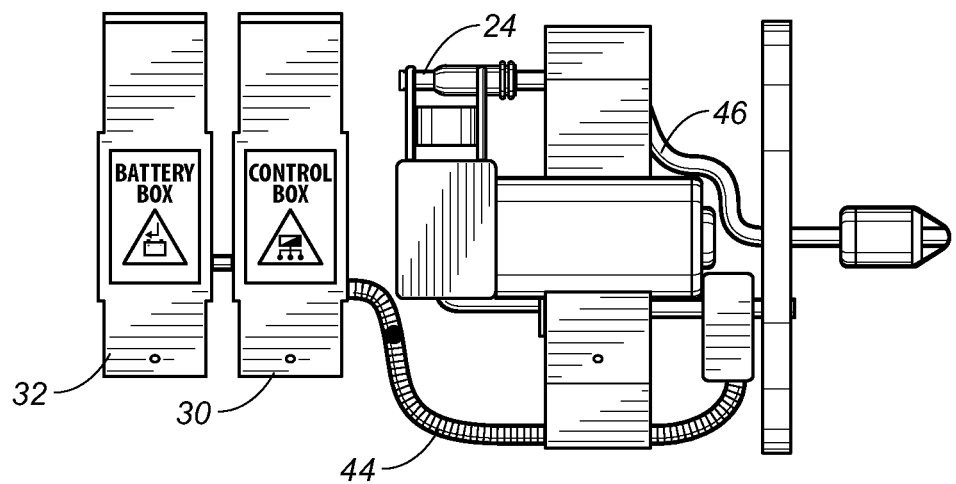
FIG. 4 is a side view of the interior components of the scraper of the present invention.

FIG. 4 shows the control system 30, the battery compartment 32, the pump 24 (or compressor or nitrogen cylinder in a gas line), the interconnecting tubing 46 and the electrical corrugated conduit 44 that brings power to the pump 24. All of these components are supported by brackets which are bolted to the scraper body 48.

Figure 5:
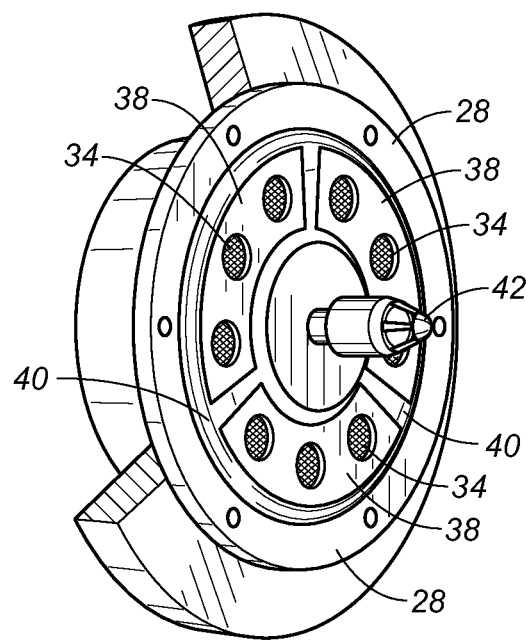
FIG. 5 is an isolated perspective view of the fluid intake side of the scraper of the present invention.

FIG. 5 shows details of the fluid intake system that consists of a set of three metallic islands 38 of three intake nozzles 34 each. Prior to starting the fluid release through the pilot operated relief valve 42, the pump 24 suctions the fluid through the intake nozzles 34. The fluid passes through the filter chamber filled with coalescent filter cartridges 52 to end up in the reservoir tank 56. The filters 52 are sufficient to keep particles of fifty microns away from the reservoir tank 56. The intake system can also work in reverse mode expelling fluid from the tank 56 if necessary.

Figure 6:
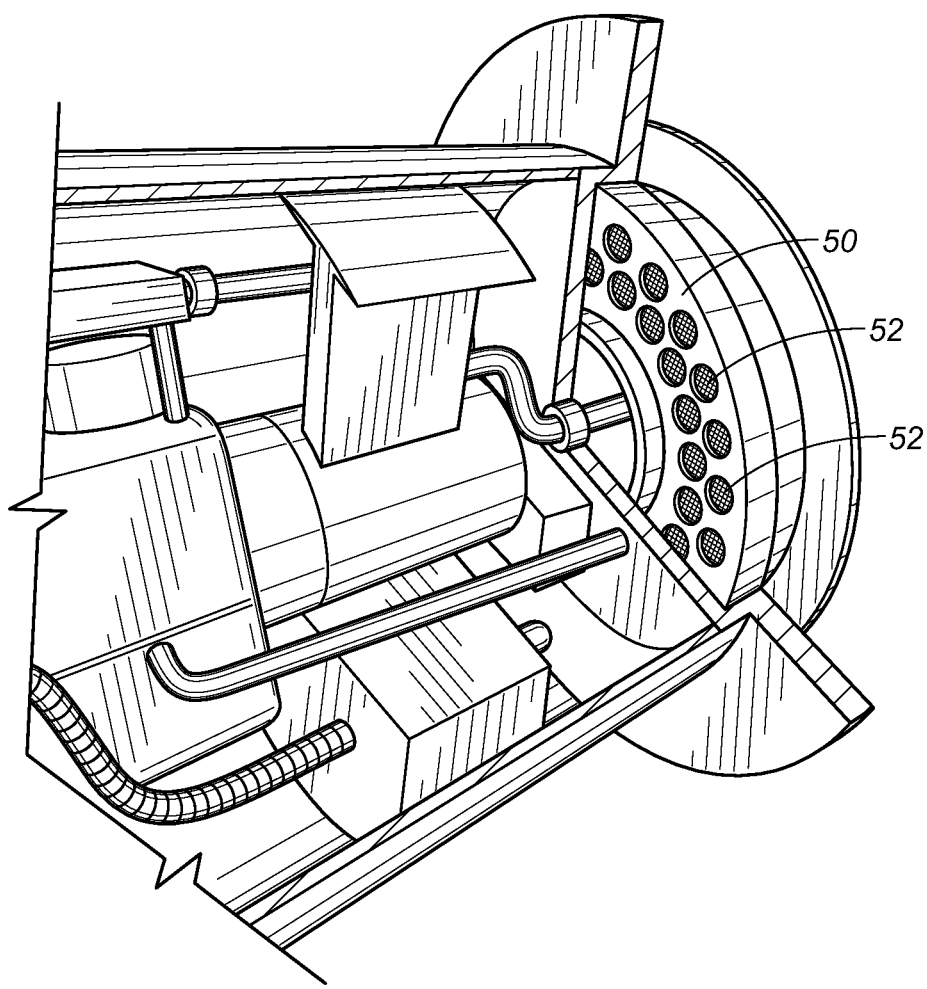
FIG. 6 is a perspective view of the interior of the scraper of the present invention showing the details of the filter chamber.

FIG. 6 shows details of the filter chamber 50 without its back cover plate showing the plurality of coalescent filter cartridges 52.

The method of the present invention involves tracking a scraper within a pipeline. The method includes the following steps. First, the scraper is moved along a path in the pipeline such that the scraper produces an acoustic signal. Next, the produced acoustic signal is sensed by at least a pair of acoustic sensors positioned in spaced relation along the pipeline. The produced acoustic signals are then time-stamped. Finally, the location of the scraper is calculated based on the time-stamped sensed produced acoustic signal and a velocity of sound in the fluid in the pipeline. The acoustic signal may be a transient pressure wave produced solely by the movement of the scraper through the pipeline. Alternatively, the acoustic signal may also be a pressure signal produced by a mechanism positioned on the scraper as described above.

The foregoing disclosure and description of the invention is illustrative and explanatory thereof. Various changes in the details of the described method can be made without departing from the true spirit of the invention. The present invention should only be limited by the following claims and their legal equivalents.

We claim:

1. A method for tracking a scraper within a pipeline comprising the steps of:

moving the scraper along a path in the pipeline such that said scraper produces an acoustic signal;

sensing the acoustic signal produced by the scraper by at least a pair of acoustic sensors positioned in spaced relation along the pipeline;

time-stamping the sensed acoustic signal; and calculating a location of the scraper based on the time-stamped sensed acoustic signal.

2. The method of claim 1, said acoustic signal being a transient pressure wave produced by the movement of the scraper.

3. The method of claim 1, said acoustic signal being a pressure signal produced by a mechanism positioned on said scraper.

* * * * *